United States Patent
Merchant et al.

(10) Patent No.: US 11,014,944 B2
(45) Date of Patent: May 25, 2021

(54) PROCESS FOR THE PREPARATION OF CRISABOROLE AND ITS INTERMEDIATES

(71) Applicant: Halcyon Labs Private Limited, Mumbai (IN)

(72) Inventors: Rupa Sudhir Merchant, Mumbai (IN); Aditya Sudhir Merchant, Mumbai (IN); Piyushkumar Bhikhalal Limbad, Ahmedabad (IN); Akshay Madhubhai Pansuriya, Amreli (IN); Bhavin Madhavjibhai Vavaiya, Ahmedabad (IN); Jasmin Jaysukhlal Faldu, Ahemdabad (IN)

(73) Assignee: Halcyon Labs Private Limited, Mumbai (IN)

( * ) Notice: Subject to any disclaimer, the term of this patent is extended or adjusted under 35 U.S.C. 154(b) by 0 days.

(21) Appl. No.: 16/960,122

(22) PCT Filed: Jan. 1, 2019

(86) PCT No.: PCT/IN2019/050002
§ 371 (c)(1),
(2) Date: Jul. 6, 2020

(87) PCT Pub. No.: WO2019/138422
PCT Pub. Date: Jul. 18, 2019

(65) Prior Publication Data
US 2021/0070778 A1     Mar. 11, 2021

(30) Foreign Application Priority Data
Jan. 9, 2018  (IN) .............................. 201821000974

(51) Int. Cl.
*C07F 5/02* (2006.01)
*C07C 253/30* (2006.01)
*C07C 255/54* (2006.01)

(52) U.S. Cl.
CPC ............ *C07F 5/025* (2013.01); *C07C 253/30* (2013.01); *C07C 255/54* (2013.01)

(58) Field of Classification Search
CPC ................................ C07F 5/025; C07C 253/30
See application file for complete search history.

(56) References Cited

U.S. PATENT DOCUMENTS

| | | | |
|---|---|---|---|
| 8,039,451 B2 | 10/2011 | Baker et al. | |
| 8,168,614 B2 | 5/2012 | Baker et al. | |
| 8,501,712 B2 | 8/2013 | Baker et al. | |
| 9,682,092 B2 | 6/2017 | Baker et al. | |
| 10,329,311 B1 * | 6/2019 | Gassa | ...................... B01J 23/42 |

OTHER PUBLICATIONS

Akama. Discovery and structure-activity study of a novel benzoxaborole anti-inflammatory agent (AN2728) for the potential topical treatment of psoriasis and atopic dermatitis. Bioorganic & Medicinal Chemistry Letters vol. 19 2009, 2129-2132.
Zekri. A solvent free and selective method for preparation of triphenylmethyl enters of alcohols and nucleosides. Bulletin of the Chemical Society of Ethiopia. Feb. 22, 2010. 299-304.
Sun. A method for the deprotection of Alkylpinacoly Boronate Esters. The Journal of Organic Chemistry. Mar. 30, 2011.
International Search Report dated Mar. 18, 2019, issued in International Application No. PCT/IN2019/050002 (3 pages).

* cited by examiner

*Primary Examiner* — Golam M Shameem
(74) *Attorney, Agent, or Firm* — Beem Patent Law Firm

(57) ABSTRACT

The present invention provides a novel and improved process for the preparation of Crisaborole of Formula (I) and its pharmaceutically acceptable salts. The present invention also provides novel intermediates and process for the preparation of intermediates used in the preparation of Crisaborole. The present invention also provides an improved process for the preparation of Crisaborole and pharmaceutically acceptable salts thereof, that is commercially and industrially scalable.

7 Claims, No Drawings

PROCESS FOR THE PREPARATION OF CRISABOROLE AND ITS INTERMEDIATES

CROSS-REFERENCE TO RELATED APPLICATIONS

This application claims benefit of PCT/IN2019/050002 filed Jan. 1, 2019, which claims benefit of India Patent Application No. 201821000974, filed Jan. 9, 2018, each of which is incorporated by reference in its entirety.

FIELD OF THE INVENTION

The present invention provides a novel and improved process for the preparation of Crisaborole of Formula (1) and its pharmaceutically acceptable salts. The present invention also provides novel intermediates and process for the preparation of intermediates used in the preparation of Crisaborole. The present invention also provides an improved process for the preparation of Crisaborole and pharmaceutically acceptable salts thereof, that is commercially and industrially scalable.

BACKGROUND OF THE INVENTION

Crisaborole is a non-steroidal PDE4 inhibitor useful in the treatment of inflammatory skin diseases, including mild to moderate atopic dermatitis and psoriasis. Crisaborole is the first topical ointment PDE4 inhibitor for mild to moderate atopic dermatitis (AD) for patients two years of age and older and is recommended for twice daily application to the affected areas for about 28 days and up to an additional 48 weeks. Crisaborole, chemically known as 5-(4-cyanophenoxy)-1,3-dihydro-1-hydroxy-2,1-benzoxaborole, is represented by compound of formula I:

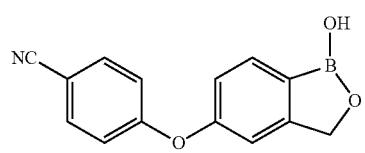

(I)

U.S. Pat. Nos. 8,039,451, 8,168,614, 8,501,712 cover the compound and various method of treatments thereof. All references cited herein are incorporated in its entirety and for all purposes.

Crisaborole was first time disclosed in U.S. Pat. No. 8,039,451. US '451 discloses various process for the preparation of Crisaborole and one of them is depicted herein below in Scheme-1.

Scheme-1

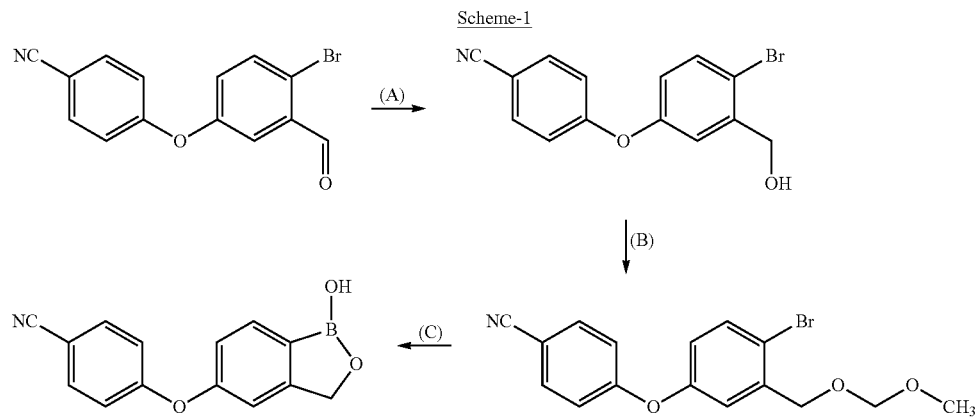

US '451 discloses a process for the preparation of Crisaborole, which comprises a) reduction of 4-(4-bromo-3-formyl-phenoxy)-benzonitrile the presence of sodium borohydride provides 4-(4-bromo-3-hydoxymethyl-phenoxy)-benzonitrile b) alkylation of the said alcohol intermediate with chloromethyl methyl ether in the presence of suitable base provides alkyl protected compound and c) Metallation and Boronylation of the alkyl protected compound with trimethyl borate in the presence of n-butyl lithium at −78° C. in dry THF provides Crisaborole.

Bioorg. Med. Chem. Lett. 2009, 19, 2129-2132 discloses another process for the preparation of Crisaborole, which comprises 1) the reaction of 2-bromo-5-hydroxy Benzaldehyde with ethylene glycol is provided the acetal protected compound b) the reaction of acetal protected compound with 4-cyano-fluorobenzene is provided 4-(4-bromo-3-formyl-phenoxy)-benzonitrile and c) boronylation of the obtained aldehyde compound is carried out in the presence of n-butyl lithium and trialkyl borate at −78° C. in dry THF, which further undergoes deprotection in the presence of hydrochloric acid and spontaneous cyclization to provide Crisaborole.

Scheme-2

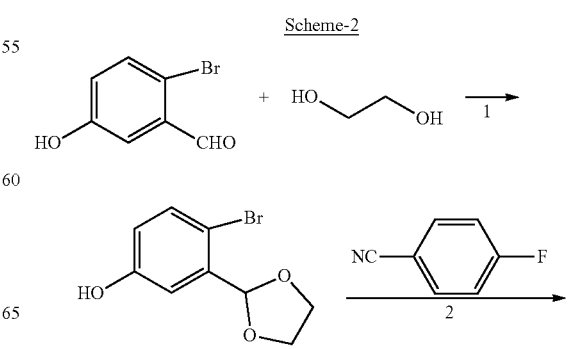

-continued

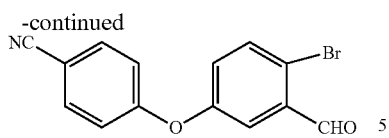

↓3

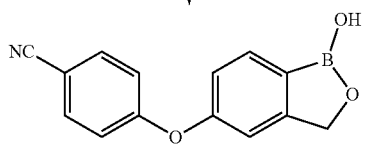

The major disadvantage associated with the prior art processes are:
- Use of hazardous reagent like n-butyl lithium may cause for many inconvenient reactions such as fire or explosion, irritation or toxic fumes in a fire, it produces lower yield and higher impurities. Further, due to the explosive nature of n-butyl lithium, it is difficult to handle at plant scale.
- Use of n-butyl lithium and trialkyl borate, which invokes the formation of dimer and trimer impurities. The removal of dimer and trimer impurities needs an additional step of purification, which increases the overall cost of synthesis.
- Use of laborious Flash column chromatographic purification, which not only increases the consumption of solvent but also difficult to handle on the commercial scale, including the obvious practical limitations of column chromatography on industrial scale.
- Use of cryogenic temperature of −78° C., which is difficult to attain during commercial production.

The complexity of the known processes for the preparation of the Crisaborole and its intermediates are used expensive, corrosive/toxic reagents, drastic reactions conditions and purification by flash column chromatography. The above process reagents or conditions are difficult to apply for industrially scale up.

Hence, there is consequently a need for a novel process for the preparation of Crisaborole and its intermediates. The above disadvantages are overcome by the present invention provides an industrial viable process for the preparation of Crisaborole (I) and this method is simple and efficient, wide-ranging sources of raw materials, synthetic route is simple, easy operation, mild reaction conditions, high yield with low synthesis cost, easy post-processing, eco-friendly and suitable for industrial production.

OBJECT OF THE INVENTION

The principal object of the present invention is to provide an improved process for the preparation of Crisaborole, which alleviates the drawbacks of prior art processes and provide an alternative process for the preparation of Crisaborole.

It is another object of the present invention to provide a cost effective and industrially feasible process for the preparation of Crisaborole, which minimizes the formation of by products and gives Crisaborole in high yield and purity.

It is still another object of the present invention to provide a novel economically significant process for the preparation of Crisaborole or its pharmaceutically acceptable salts for large scale industrial preparation.

It is still another object of the present invention to provide an improved and commercially viable process for the preparation of Crisaborole via novel intermediates of Formula (IV), (III) and (II).

SUMMARY OF THE INVENTION

In one aspect, the present invention provides an improved process for the preparation of Crisaborole of formula (1) comprising the steps of:

a) treating 4-(4-halo-3-hydroxymethyl-phenoxy)-benzonitrile of formula (V) with trityl chloride in the presence of base and suitable solvent to give 4-{4-halo-3-[(trityloxymethyl)]phenoxy}benzonitrile of formula (IV);

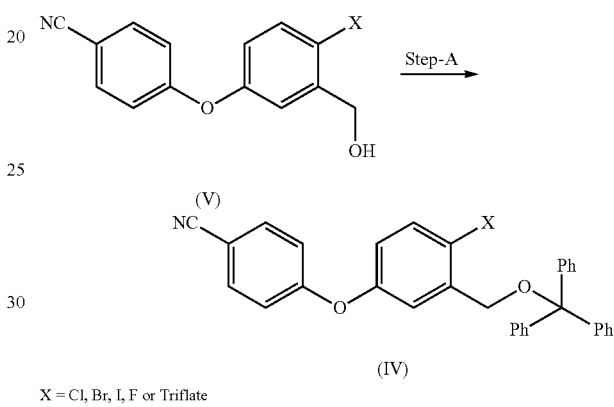

X = Cl, Br, I, F or Triflate b) reacting of compound of formula (IV) with pinacolborane or bis(pinacolato)diboron in the presence of a transition metal catalyst and a base in suitable solvent to give 4-[4-(4,4,5,5-tetramethyl-[1,3,2]dioxaborolan-2-yl) 3-trityloxymethyl-phenoxy]-benzontirile of formula (III);

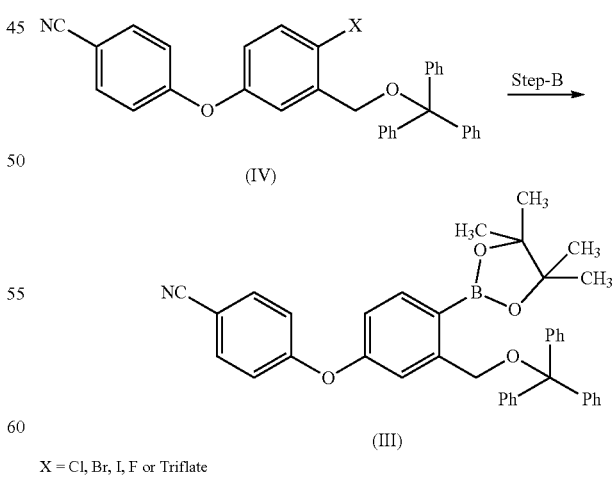

X = Cl, Br, I, F or Triflate c) optionally transesterifying the compound of formula (III) with diethanolamine in suitable solvent to provide the compound of formula (II);

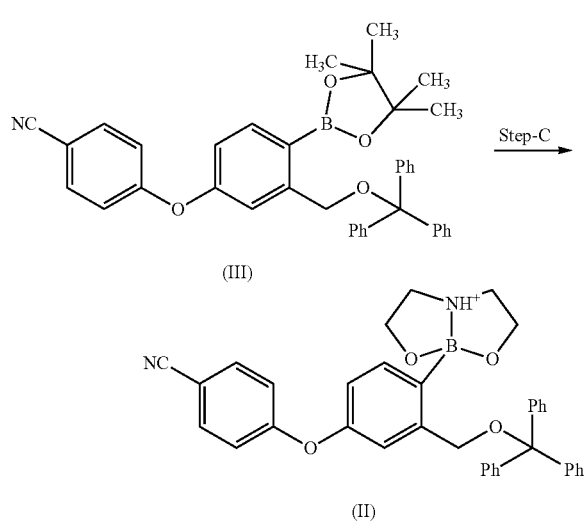

(III)

(II)

d) deprotecting and cyclizing the compound of formula (II) or (III) in the presence of suitable acid and solvent to give Crisaborole of formula (I); and

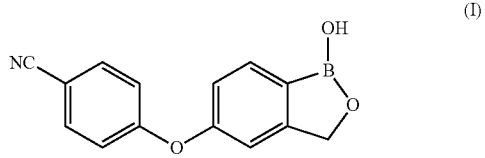 [SMILES: N#Cc1ccc(Oc2ccc3c(c2)COB3O)cc1]

(I)

e) optionally purifying Crisaborole of formula (I).

In another aspect, the present invention provides an improved process for the preparation of Crisaborole of formula (I) comprising the steps of:
a) treating 4-(4-halo-3-hydroxymethyl-phenoxy)-benzonitrile of formula (V) with trityl chloride in the presence of base and suitable solvent to give 4-{4 halo-3-[(trityloxymethyl)]phenoxy}benzonitrile of formula (IV);
b) reacting of compound of formula (IV) with pinacolborane or bis(pinacolato)diboron in the presence of a transition metal catalyst and a base in suitable solvent to give 4-[4-(4,4,5,5-tetramethyl-[1,3,2]dioxaborolan-2-yl)-3-trityloxymethyl-phenoxy]-benzontirile of formula (III);
c) deprotecting and cyclizing the compound of formula (III) in the presence of suitable acid and solvent to give Crisaborole of formula (I); and
d) optionally purifying Crisaborole of formula (I).

In yet another aspect, the present invention provides an improved process for the preparation of Crisaborole of formula (I) comprising the steps of:
a) treating 4-(4-halo-3-hydroxymethyl-phenoxy)-benzonitrile of formula (V) with trityl chloride in the presence of base and suitable solvent to give 4-{4-halo-3-[(trityloxymethyl)]phenoxy}benzonitrile of formula (IV);
b) reacting of compound of formula (IV) with pinacolborane or bis(pinacolato)diboron in the presence of a transition metal catalyst and a base in suitable solvent to give 4-[4-(4,4,5,5-tetramethyl-[1,3,2]dioxaborolan-2-yl)-3-trityloxymethyl-phenoxy]-benzontirile of formula (III);
c) transesterifying the compound of formula (III) with diethanolamine in suitable solvent to provide the compound of formula (II);
d) deprotecting and cyclizing the compound of formula (II) in the presence of suitable acid and solvent to give Crisaborole of formula (I); and
e) optionally purifying Crisaborole of formula (I).

In another aspect, the present invention provides an improved process for the preparation of Crisaborole of formula (I) comprising the steps of:
a) deprotecting and cyclizing the compound of formula (II) in the presence of suitable acid and solvent to give Crisaborole of formula (I); and
b) optionally purifying Crisaborole of formula (I).

In another aspect, the present invention provides an improved process for the preparation of Crisaborole of formula (I) comprising the steps of:
a) deprotecting and cyclizing the compound of formula (II) in the presence of suitable acid and solvent to give Crisaborole of formula (I); and
b) optionally purifying Crisaborole of formula (1).

In yet another aspect, the present invention provides a process for preparing highly pure Crisaborole comprising:
a) reacting Crisaborole with mono-ethanolamine in suitable solvent to obtain ethanolamine salt of Crisaborole,
b) isolating mono-ethanolamine salt of Crisaborole obtained in step a), and
c) converting the obtained mono-ethanolamine salt of Crisaborole to a highly pure Crisaborole.

In yet another aspect, the present invention provides novel intermediate of compound of formula (IV);

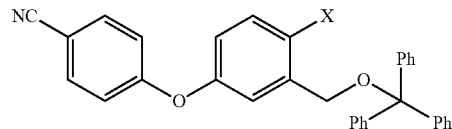

(IV)

wherein, X=chloro, bromo, iodo, fluoro or triflate.

In yet another aspect, the present invention provides the use of compound of formula (IV) for the preparation of Crisaborole.

In yet another aspect, the present invention provides novel intermediate of compound of formula (IV) in solid state, wherein X is bromo.

In yet another aspect, the present invention provides novel intermediate of compound of formula (II).

In yet another aspect, the present invention provides novel intermediate of compound of formula (III) in solid state.

In yet another aspect, the present invention provides the use of compound of formula (III) for the preparation of Crisaborole.

In yet another aspect, the present invention provides novel intermediate of compound of formula (II).

In yet another aspect, the present invention provides novel intermediate of compound of formula (II) in solid state.

In yet another aspect, the present invention provides the use of compound of formula (II) for the preparation of Crisaborole.

In yet another aspect, the present invention provides an efficient, industrially advantageous and environmentally friendly process for the preparation of Crisaborole in high overall yield and with high purity using novel intermediates.

DETAILED DESCRIPTION OF INVENTION

Reference will now be made in detail to the preferred embodiments of the invention. This invention may, however, be embodied in many different forms and should not be construed as limited to the embodiments set forth herein.

As used herein, "comprising" means the elements recited, or their equivalents in structure or function, plus any other element or elements which are not recited. The terms "having" and "including" are also to be construed as open ended unless the context suggests otherwise.

When a molecule or other material is identified herein as "pure", it generally means, unless specified otherwise, that the material has 99% purity or higher, as determined using methods conventional in the art such as high performance liquid chromatography (HPLC), gas chromatography (GC), or spectroscopic methods. In general, this refers to purity with regard to unwanted residual solvents, reaction by-products, impurities, and unreacted starting materials.

In general, the present invention provides a process for the preparation of Crisaborole of formula (I) comprising the steps of:

a) treating 4-(4-halo-3-hydroxymethyl-phenoxy)-benzonitrile of formula (V) with trityl chloride in the presence of base and suitable solvent to give 4-{4-halo-3-[(trityloxymethyl)]phenoxy}benzonitrile of formula (IV);

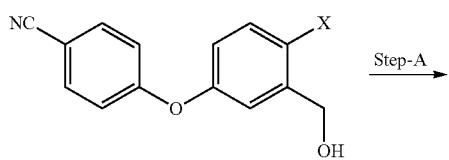

(V)

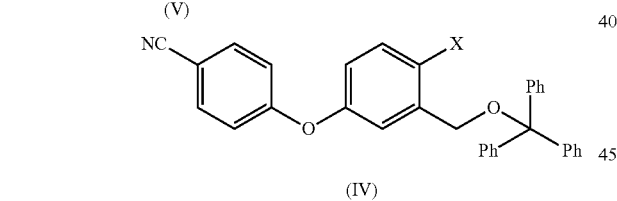

(IV)

X = Cl, Br, I, F or Triflate b) reacting of compound of formula (IV) with pinacolborane or bis(pinacolato)diboron in the presence of a transition metal catalyst and a base in suitable solvent to give 4-[4-(4,4,5,5-tetramethyl-[1,3,2]dioxaborolan-2-yl) 3-trityloxymethyl-phenoxy]-benzontirile of formula (II);

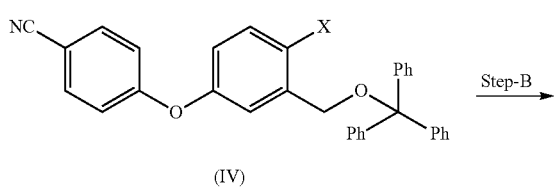

(IV)

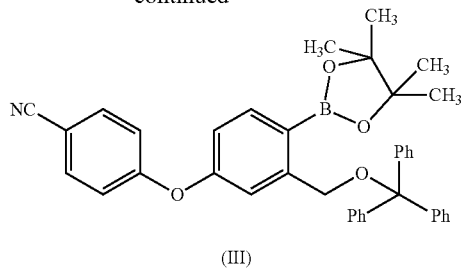

(III)

X = Cl, Br, I, F or Triflate c) optionally transesterifying the compound of formula (III) with diethanolamine in suitable solvent to provide the compound of formula (II);

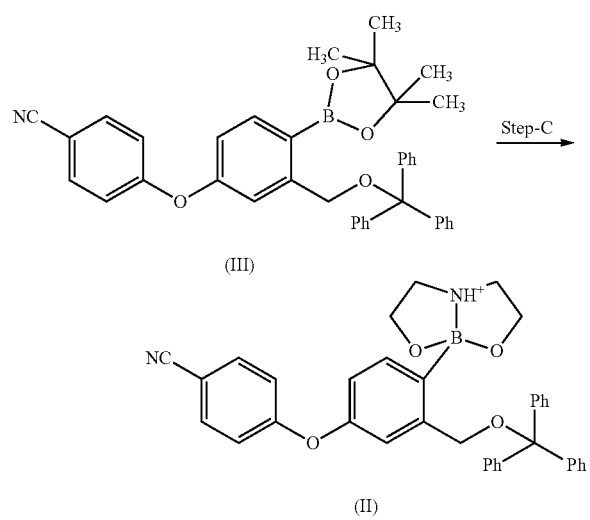

(III)

(II)

d) deprotecting and cyclizing the compound of formula (II) or (III) in the presence of suitable acid and solvent to give Crisaborole of formula (I); and

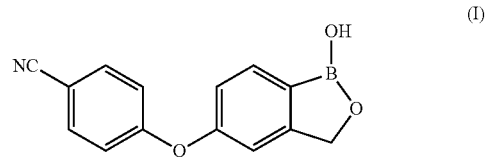 [SMILES: N#Cc1ccc(Oc2ccc3c(c2)COB3O)cc1]

(I)

e) optionally purifying Crisaborole of formula (I).

Processes for obtaining the compound of formula (V) can be according to the literature methods.

According to the present invention, step a) involves the reaction of compound of formula (V) and trityl chloride in the presence of base and suitable solvent to provide the compound of formula (IV). The reaction of step a) can be carried out at any suitable range of temperature generally at 20° C.-140° C., preferably at 20° C.-80° C. over a period of about 1 to 10 hours, preferably for 2 to 8 hours.

The suitable solvent used for the above step a) is selected from the group comprising of alcohols such as methanol, ethanol, propanol, isopropanol and butanol and the like; chlorinated hydrocarbons such as methylene chloride, chloroform and the like; ethers such as diisopropyl ether, methyl tert-butyl ether, dioxane, tetrahydrofuran and the like; esters such as ethyl acetate, isopropyl acetate and the like; ketone solvent such as methyl isobutyl ketone, acetone and the like; polar aprotic solvents such as dimethylformamide, dimethyl sulfoxide, N-methylpyrrolidone, and water or mixture thereof.

The suitable base used for the above reaction step a) is selected from organic or inorganic base, depending upon the class of solvent. The organic base is selected from the group comprising of triethylamine, diisopropylamine, diisopropylethylamine, piperidine, pyridine N-methyl morpholine N, N-dimethylbenzylamine, picoline, lutidine and the like; wherein the inorganic base is selected from the group comprising of metal carbonate such as lithium carbonate, sodium carbonate, potassium carbonate, barium carbonate, calcium carbonate and magnesium carbonate; metal bicarbonate such as sodium bicarbonate, potassium bicarbonate, barium bicarbonate, calcium bicarbonate and magnesium bicarbonate and metal hydroxide such as sodium hydroxide, potassium hydroxide, barium hydroxide, calcium hydroxide and magnesium hydroxide.

The compound of formula (IV) can be isolated and/or purified by any conventional method known to one of skill in the art.

According to the present invention, step b) involves the reaction of compound of formula (IV), wherein X is as defined above, with pinacolborane or bis(pinacolato)diboron in the presence of a transition metal catalyst and a base in suitable solvent to give the compound of formula (II). The reaction of step b) can be carried out at any suitable range of temperature generally at 20° C.-200° C., preferably at 70° C.-120° C. over a period of about 5 to 25 hours. In place of pinacolborane or bis(pinacolato)diboron other suitable borylation reagent known in the art can be used.

The transition metal catalyst as used in step b) comprises one or more phosphine ligands which are complexing the transition metal. Most preferred are palladium phosphine complexes like Pd(PPh3), PdCl2(dppf). CH2Cl2, and related palladium catalysts which are complexes of phosphine ligands like P(i-Pr)3, P(cyclohexyl)3, 2-dicyclohexylphosphino-2',4',6'-triisopropylbiphenyl (X-Phos) 2-dicyclohexyl phosphino-2',6'-dimethoxybiphenyl (S-Phos), (2,2''-bis(diphenylphosphino)-1,1''-binaphthyl) (BINAP) or Ph2P(CH2),PPh2 with n is 2 to 5. More preferred is PdCl2(dppf).CH2Cl2 i.e. [1,1'-Bis(diphenylphosphino)ferrocene] dichloropalladium (II) complex with dichloromethane.

The preferred base as used in step b) should be able to catalyse a borylation reaction. Examples are potassium acetate, potassium phosphate, potassium carbonate, sodium or lithium analogues of these potassium salts, trimethylamine and triethylamine. More preferred is potassium acetate.

The suitable solvent used for the above step b) is selected from the group comprising polar aprotic solvent such as acetonitrile, tetrahydrofuran, dioxane, dimethylformamide, dimethylacetamide, dimethyl sulfoxide, hexamethylphsophoric triamide, sulforan, N-methylpyrrolidone and the like; aromatic hydrocarbon solvent such as benzene, toluene, xylene, ethylbenzene, diethylbenzene, styrene, vinyltoluene, divinylbenzene, alpha-methylstyrene or mixture thereof.

According to present invention, step c) involves the transesterification of compound of formula (III) with diethanolamine in suitable solvent to provide the compound of formula (II).

The reaction of step c) can be carried out at any suitable range of temperature generally at 20° C.-80° C., preferably at 20° C.-50° C. over a period of about 5 to 25 hours.

The transesterification reaction of step c) alleviates the need of further isolation and/or purification of compound of formula (III) i.e. compound of formula (I) can be in-situ converted into Crisaborole (I) via transesterification.

The transesterification reaction of step c) is carried out in the same solvent as used for the preparation of compound of formula (I) i.e. step b).

According to the present invention, step d) involves deprotection and cyclization of the compound of formula (II) or (III) in the presence of suitable acid and solvent to give Crisaborole of formula (1). The reaction of step d) can be carried out at any suitable range of temperature generally at 20° C.-80° C., preferably at 20° C.-50° C. over a period of about 5 to 25 hours.

In step d) the deprotection and cyclization of compound of formula (II) or (III) is carried out in the single steps in the presence of suitable acid and solvent. Suitable acids are selected from the group consisting of organic carboxylic acids, sulfonic acids, and inorganic acids. The organic carboxylic acid may be formic acid, oxalic acid, acetic acid, trimethyl acetic acid or trifluoroacetic acid, preferably acetic acid. The sulfonic acid may be methanesulfonic acid or p-toluene sulfonic acid. The inorganic acid may be hydrochloric acid, hydrobromic acid, sulfuric acid, pivalic acid or phosphoric acid, preferably hydrochloric acid.

The suitable solvent used for the above step d) is selected from the group comprising of alcohols such as methanol, ethanol, propanol, isopropanol and butanol and the like; chlorinated hydrocarbons such as methylene chloride, chloroform and the like; ethers such as diisopropyl ether, methyl tert-butyl ether, dioxane, tetrahydrofuran and the like; esters such as ethyl acetate, isopropyl acetate and the like; ketone solvent such as methyl isobutyl ketone, acetone and the like; polar aprotic solvents such as dimethylformamide, dimethyl sulfoxide, N-methylpyrrolidone, and water or mixture thereof.

The deprotection and cyclization of compound of formula (II) or (III) of step d) may also be carried out in the presence of quaternary ammonium salt selected from a group comprising of tetrabutylammonium chloride (TBAC), tetrabutylammonium bromide (TBAB), tetrabutylammonium iodide (TBAI), tetrabutyl ammonium sulfate, cetyl trimethyl ammonium iodide, tetraethylammonium chloride (TEAC), tetrapropylammonium bromide (TPAB), tetrabutylammonium fluoride (TBAF), tetrapropylammonium perruthenate (TPAP), benzyltrimethylammonium chloride (BTMAC), benzyltriethylammonium chloride (BTAC), tetrabutylammonium hydroxide (TBAH), methyltricaprylammonium chloride (MTCAC), tributylmethylammonium chloride (MTBAC) or trioctylmethylammonium chloride. Preferably quaternary ammonium salt is TBAB.

According to the present invention, step (f) comprises optional purification of Crisaborole by recrystallizing or slurring_in suitable solvent selected from the group comprising alcohols such as methanol, ethanol, propanol, isopropanol and butanol and the like; ketones such as acetone, ethyl methyl ketone, diethyl ketone, methyl isobutyl ketone, and the like; chlorinated hydrocarbons such as methylene chloride, chloroform and the like; ethers such as diisopropyl ether, methyl tert-butyl ether and the like; esters such as ethyl acetate, isopropyl acetate and the like and water or mixture thereof.

In yet another aspect, the present invention provides a process for preparing highly pure Crisaborole comprising:
  a) reacting Crisaborole with mono-ethanolamine in suitable solvent to obtain ethanolamine salt of Crisaborole, b) isolating mono-ethanolamine salt of Crisaborole obtained in step a), and c) converting the obtained mono-ethanolamine salt of Crisaborole to a highly pure Crisaborole.

The process for preparing Crisaborole ethanolamine salt can be carried out by combining solution of Crisaborole in suitable organic solvent with ethanolamine. The organic solvent is selected from alcohols such as methanol, ethanol, propanol, isopropanol and butanol and the like; esters such as ethyl acetate, isopropyl acetate and the like and water or mixture thereof. The resulting Crisaborole ethanolamine salt can be isolated by any means known in the art including, but not limited to, filtering, centrifuging, or decanting.

The resulting Crisaborole ethanolamine salt is converted back to the Crisaborole by combining the Crisaborole ethanol amine salt with the solution of suitable acid. Preferably, the solution of suitable acid is prepared by adding the Tartaric acid in water.

In an embodiment pure Crisaborole obtained according to the present invention, is having purity more than 99%.

The processes for the preparation of Crisaborole and its intermediates disclosed herein have the following advantages over the processes described in the prior art:

i) the process involves the use of novel intermediate compound of compound of formula (IV), (III) and (II);

ii) the overall yield of the Crisaborole and its key intermediate is increased and the purity of the product is increased without additional purifications and column schromatographic purifications;

iii) the process avoids the use of highly flammable reagent like n-butyl lithium;

iv) the process avoids the use of tedious and cumbersome procedures multiple extractions using different solvents, column chromatographic purifications, multiple isolation/recrystallizations;

vii) the processes involve, easy work-up methods and simple isolation processes, and there is a reduction in chemical waste.

The process details of the invention are provided in the examples given below, which are provided by way of illustration only and therefore should not be construed to limit the scope of invention.

EXAMPLES

Example-1

Preparation of 4-{4-bromo-3-[(trityloxymethyl)] phenoxy}benzonitrile [Compound of Formula (IV), Wherein X=Br]

Trityl chloride (68.75 gm) was added to a stirred solution of methylene chloride (100 ml) at 25° C.-30° C. DIPEA (45.8 ml) was added to the reaction mixture and heated to 40° C.-45° C. The solution of 2-bromo-5-(4-cyanophenoxy) benzyl alcohol (50 gm) in methylene chloride (400 ml) was added to the reaction mixture at 40° C.-45° C. over a 1 hour period and stirred for 5 hours at the same temperature. The reaction progress was monitored by thin layer chromatography (TLC). After completion of the reaction, reaction mixture was cooled to 25° C.-30° C. and water (200 ml) was added slowly to the reaction mixture and stirred for 15 to 20 minutes. Organic layer was added with water and stirred for 15 to 20 minutes. The phases were separated and organic phase was distilled under vacuum at 40° C.-45° C. Methanol (250 ml) was added to the obtained reaction mass and heated up to the reflux temperature for 2 hour. The reaction mixture was cooled to 25° C.-30° C., stirred for 30 minutes and filtered. The solid was washed with methanol (25×2 ml) and dried at 50° C. in ATD for 2 hours and further dried at 25° C.-30° C. under vacuum for 12 hrs to obtain crude 4-{4-halo-3-[(trityloxymethyl)]phenoxy}benzonitrile (85.5 gm); Purity=88%.

$^1$H NMR (CDCl3, 400 MHz) $^\delta$ (ppm): 4.235 (s, 2H), 6.806-6.834 (dd, J=8.4, 2.8 Hz, 1H), 7.051-7.073 (dd, J=6.8, 2.0 Hz, 2H), 7.211-7.309 (m, 9H), 7.439-7.463 (m, 7H), 7.545-7.552 (d, J=2.8 Hz, 1H), 7.620-7.643 (dd, J=6.8, 2.0 Hz, 2H).

Example-2

Preparation of 4-[4-(4,4,5,5-tetramethyl-(1,3,2]di-oxaborolan-2-yl)-3-trityloxy Methyl phenoxy]-benzontirile (III)

A mixture of compound of formula (IV-A) (50 gm), PdCl2(dppf)CH2Cl2 (1.49 gm), potassium acetate (26.90 gm) and bis(pinacolato)diboron (27.90 mg) in 1,4-dioxane (1000 ml) was heated at 90° C. and maintained for 25 hours. The reaction mixture cooled to 25° C.-30° C., filtered and washed the bed with 1,4-dioxan (50 ml). The solvent was distilled under vacuum at 50° C.-60° C. and obtained mass was added with isopropanol (350 ml) at 55° C.-60° C. and stirred for 30 minutes at the same temperature. The obtained mass was cooled to 25° C.-30° C. within 1-2 hrs and maintained for 1 hr. The obtained solid was filtered and washed with isopropanol (50×2 ml) and dried at 25° C. to 30° C. under vacuum for 14 hrs to obtain the title compound (42 gm); Purity=98.11%.

$^1$H NMR (CDCl3, 400 MHz) $^\delta$ (ppm): 1.165 (s, 12H), 4.490 (s, 2H), 6.904-6.930 (dd, J=8.2, 2.4 Hz, 1H), 7.102-7.125 (dd, J=7.2, 2.0 Hz, 2H), 7.213-7.303 (m, 9H), 7.449-7.467 (m, 6H), 7.626-7.655 (dd, J=6.8, 2.0 Hz, 2H), 7.666-7.672 (d, J=2.4 Hz, 1H), 7.775-7.795 (d, J=8.0 Hz, 1H).

Example-3

Preparation of Crisaborole [Compound of Formula (1)]

10.0 gm compound of formula (III) of was added to the stirred solution of methylene chloride (50 ml) at 25° C.-30° C. TBAB (0.5 gm) was added. After the addition of concentrated hydrochloric acid (30 ml), the mixture was stirred for 24 hours at 25° C.-30° C. After completion of the reaction, the phases were separated. Water (30 ml) was added to the organic layer and phases were separated. The organic layer obtained was added 200 ml water followed by aqueous sodium hydroxide (4.49 ml 30%) and stirred for 15 mins. The aqueous layer was filtered and acidified with hydrochloric acid (9.22 ml 10%) at 25° C.-30° C. The obtained solid was filtered and washed with water (10 ml) and dried at 50° C. under vacuum for 24 hrs to obtain Crisaborole (3.6 gm); Purity=99.5%.

Example-4

Preparation of Compound of Formula (II)

A mixture of compound of formula (IV-A) (50 gm), PdCl2(dppf). CH2Cl2 (1.49 gm), potassium acetate (26.9 gm) and bis(pinacolato)diboron (27.9 gm) in 1,4-dioxane (1000 ml) was heated at 90° C. and maintained for 25 hours. The reaction mixture was cooled to 25° C.-30° C., filtered and washed the bed with 1,4-dioxan (50 ml). Diethanolamine (19.2 gm) was added and stirred for 24 hrs at 25° C.-30° C. The solid was filtered, washed with 1,4-dioxane (50 ml) and dried at 25° C. to 30° C. under vacuum for 24 hrs to obtain the compound of formula (U) (40 gm); purity=99.88%.

$^1$H NMR (CDCl3, 400 MHz) $^δ$ (ppm): 2.543-2.573 (m, 2H), 2.766-2.852 (m, 2H), 3.700-3.754 (m, 2H), 3.931-3.991 (m, 2H), 4.306 (s, 2H), 6.377 (s, 1H), 6.952-6.957 (d, J=2.0 Hz, 1H), 6.987-6.993 (d, J=2.4 Hz, 1H), 7.011-7.033 (d, J=8.8 Hz, 2H), 7.252-7.430 (m, 15H), 7.573-7.595 (d, J=8.8 Hz, 2H), 7.850-7.870 (d, J=8.0 Hz, 1H)

Example-5

Preparation of Crisaborole (Compound of Formula (I)]

10.0 gm compound of formula (II) of was added to the stirred solution of methylene chloride (50 ml) at 25° C.-30° C. TBAB (0.5 gm) was added. After the addition of concentrated hydrochloric acid (30 ml), the mixture was stirred for 24 hours at 25° C. was 30° C. After completion of the reaction, the phases were separated. Water (30 ml) was added to the organic layer and phases were separated. The obtained organic layer was cooled to 5° C.-10° C. The resulting solution was diluted with aqueous sodium hydroxide (4.59 ml 30%) at 5° C.-10° C. and stirred for 15 minutes. The obtained solid was filtered and washed with methylene chloride (10 ml) and suck dried for 20 minutes. The wet cake was added to the water (180 ml) and stirred at 25° C.-30° C. for 30 minutes. The obtained solution was filtered and acidified with hydrochloric acid (9.43 ml 10%) at 25° C.-30° C. The obtained solid was filtered and washed with water (10 ml) and dried at 50° C. under vacuum for 24 hrs to obtain Crisaborole (3.9 gm); Purity=99.4%.

Example-6

Preparation of Crisaborole Ethanolamine Salt

Crisaborole crude (2.0 gms) was added to methanol (40 ml) and stirred at room temperature for 15 minutes to obtain the clear solution. To this clear solution ethanol amine (0.73 gMs) was added and the reaction mixture was stirred at 50° C. for 60 minutes. The reaction mass was cooled to 25° C. to 30° C. and stirred for 60 minutes. The obtained solid was filtered and washed with methanol and dried under vacuum at 50° C. to 55° C. for 6 hours to obtain the Crisaborole ethanol amine salt (1.95 gms) (HPLC purity 99.90%).

$^1$H NMR (DMSO-d6, 400 MHz) $^δ$ (ppm): 2.501-2.505 (s, 2H), 3.768-3.799 (t, 2H), 4.689 (s, 2H), 5.795 (s, 2H), 6.858-6.881 (t, 2H), 7.023-7.045 (d, 2H), 7.400-7.419 (d, 2H), 7.786-7.808 (d, 2H).

Example-7

Preparation of Crisaborole from Crisaborole Ethanolamine Salt

A solution of L-tartaric acid (1.94 gms) was prepared in water (28.5 ml) and was heated to 50-55° C. Crisaborole ethanol amine salt (1.9 gms) was added portion wise to aqueous solution of L-tartaric acid at the 50-55° C. in 1 hours and the reaction mass was further maintained at same temperature for 1 hour. The obtained solid was filtered, washed with water and dried under vacuum to obtain the tittle compound Crisaborole (1.62 gms) (HPLC purity 99.91%).

We claim:

1. A process for preparation of crisaborole of formula (I) comprising steps of:

a) treating 4-(4-halo-3-hydroxymethyl-phenoxy)-benzonitrile of formula (V) with trityl chloride in presence of a base and a suitable solvent to give 4-{4-halo-3 [(trityloxymethyl)]phenoxy}benzonitrile of formula (IV);

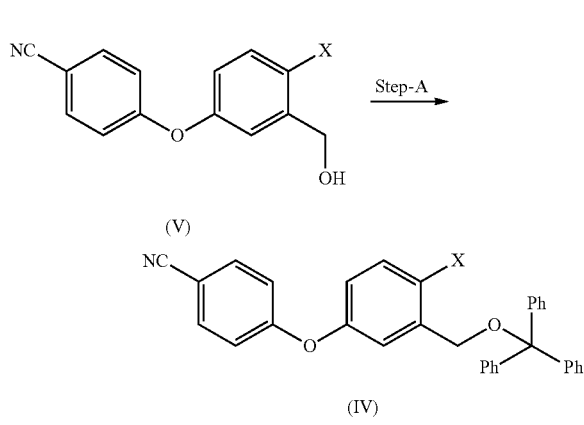

X = Cl, Br, I, F or Triflate b) reacting of the compound of formula (IV) with pinacolborane or bis(pinacolato)diboron in presence of a transition metal catalyst and the base in suitable solvent to give 4-[4-(4,4,5,5-tetramethyl-(1,3,2]dioxaborolan-2-yl) 3-trityloxymethyl-phenoxy]-benzontirile of formula (III);

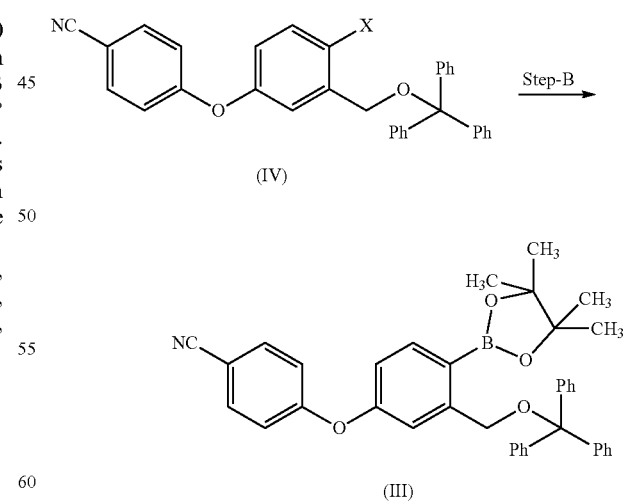

X = Cl, Br, I, F or Triflate c) optionally transesterifying the compound of formula (III) with diethanolamine in suitable solvent to provide a compound of formula (II);

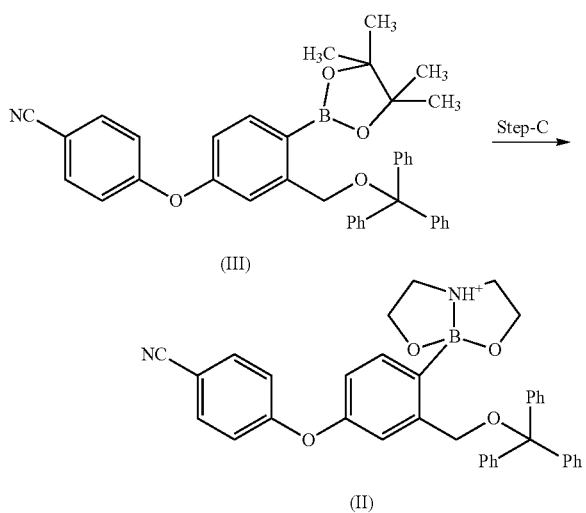

d) deprotecting and cyclizing the compound of formula (II) or (III) in presence of a suitable acid and solvent to give the crisaborole of formula (I); and

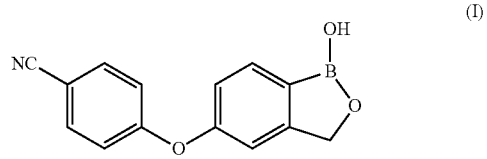 [SMILES: N#Cc1ccc(Oc2ccc3c(c2)COB3O)cc1]

e) optionally purifying the crisaborole formula (I).

2. The process according to claim 1, wherein solvent used in step a) or step d) is selected from a group consisting of methanol, ethanol, propanol, isopropanol, butanol, methylene chloride, chloroform, diisopropyl ether, methyl tert-butyl ether, dioxane, tetrahydrofuran, ethyl acetate, isopropyl acetate, methyl isobutyl ketone, acetone, dimethylformamide, dimethyl sulfoxide, N-methylpyrrolidone, water, and mixtures thereof.

3. The process according to claim 1, wherein the base used in step a) is selected from a group consisting of triethylamine, diisopropylamine, diisopropylethylamine, piperidine, pyridine N- methyl morpholine N, N-dimethylbenzylamine, picoline, lutidine, lithium carbonate, sodium carbonate, potassium carbonate, barium carbonate, calcium carbonate, magnesium carbonate, sodium hydroxide, potassium hydroxide, barium hydroxide, calcium hydroxide, and magnesium hydroxide.

4. The process according to claim 1, wherein the transition metal catalyst used in step b) is selected from a group consisting of $Pd(PPh_3)_4$, $PdCl_2(dppf).CH_2Cl_2$, P(i-Pr), P(cyclohexyl)$_3$, 2-dicyclohexylphosphino-2',4',6'-triisopropylbiphenyl (X-Phos), 2-dicyclohexyl phosphino 2',6'-dimethoxybiphenyl (S-Phos), (2,2"-bis(diphenylphosphino)-1,1" binaphthyl) (BINAP), and Ph2P(CH2),PPh2 with n is 2 to 5.

5. The process according to claim 1, wherein the base used in step b) is selected from a group consisting of potassium acetate, potassium phosphate, potassium carbonate, trimethylamine, and triethylamine.

6. The process according claim 1, wherein the suitable solvent used in step b) or step c) is selected from a group consisting of acetonitrile, tetrahydrofuran, dioxane, dimethylformamide, dimethylacetamide, dimethyl sulfoxide, hexamethylphsophoric triamide, sulforan, N-methylpyrrolidone, benzene, toluene, xylene, ethylbenzene, diethylbenzene, styrene, vinyltoluene, divinylbenzene, alpha-methylstyrene, and mixtures thereof.

7. The process according to claim 1, wherein the acid used in step d) is selected from a group consisting of formic acid, oxalic acid, acetic acid, trimethyl acetic acid, trifluoroacetic acid, methanesulfonic, p-toluene sulfonic acid, hydrochloric acid, hydrobromic acid, sulfuric acid, pivalic acid, and phosphoric acid.

* * * * *